(12) United States Patent
Koss et al.

(10) Patent No.: US 11,957,597 B2
(45) Date of Patent: *Apr. 16, 2024

(54) SPINAL DISC IMPLANT AND DEVICE AND METHOD FOR PERCUTANEOUS DELIVERY OF THE SPINAL DISC IMPLANT

(71) Applicant: Percheron Spine, LLC, Miromar Lakes, FL (US)

(72) Inventors: Scott Koss, Delafield, WI (US); Bob Gessert, Miromar Lakes, FL (US)

(73) Assignee: Percheron Spine, LLC, Miromar Lakes, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/821,729

(22) Filed: Aug. 23, 2022

(65) Prior Publication Data

US 2022/0395380 A1    Dec. 15, 2022

Related U.S. Application Data

(63) Continuation of application No. 16/961,758, filed as application No. PCT/US2018/013578 on Jan. 12, 2018, now Pat. No. 11,419,733.

(51) Int. Cl.
*A61F 2/44*     (2006.01)
*A61F 2/46*     (2006.01)
*A61F 2/30*     (2006.01)

(52) U.S. Cl.
CPC .............. *A61F 2/442* (2013.01); *A61F 2/441* (2013.01); *A61F 2/4611* (2013.01);
(Continued)

(58) Field of Classification Search
CPC .................. A61F 2/441; A61F 2002/4495
See application file for complete search history.

(56) References Cited

U.S. PATENT DOCUMENTS 3,875,595 A    4/1975  Froning
4,772,287 A    9/1988  Ray et al.
(Continued)

FOREIGN PATENT DOCUMENTS

EP      1229873 B1    1/2004
WO  2003039412 A1    5/2003
(Continued)

OTHER PUBLICATIONS

International Search Report and Written Opinion for related Application No. PCT/US2013/077845 dated Mar. 19, 2014 (19 Pages).
(Continued)

*Primary Examiner* — Nicholas W Woodall
(74) *Attorney, Agent, or Firm* — Inskeep IP Group, Inc.

(57) ABSTRACT

A spinal disc implant including a body defined by a plurality of interwoven or braided nitinol strands. The body includes a first end and a second end. The nitinol strands come together at the first end and are secured with a first fitting. The nitinol strands also come together at the second end and are secured with a second fitting. The second fitting can include a snare hook. The braided nitinol skeleton is internally assembled within the intervertebral disc. The implant is filled with liquid, gel or silicone when utilized as a motion preserving nucleus pulpous implant. The implant is filled with bone graft material when utilized as an inter-body fusion implant. An instrument and technique that provides a minimally invasive "needle based" solution to address degenerative disc disease with enhanced structural integrity of the spine compared to conventional surgical devices and techniques.

9 Claims, 14 Drawing Sheets

(52) U.S. Cl.
CPC .............. *A61F 2002/30003* (2013.01); *A61F 2002/30581* (2013.01); *A61F 2002/444* (2013.01); *A61F 2002/4495* (2013.01); *A61F 2002/4629* (2013.01); *A61F 2002/4635* (2013.01); *A61F 2310/00023* (2013.01)

(56) References Cited

U.S. PATENT DOCUMENTS

| | | |
|---|---|---|
| 5,108,404 A | 4/1992 | Scholten et al. |
| 5,562,736 A | 10/1996 | Ray et al. |
| 5,571,189 A | 11/1996 | Kuslich |
| 5,645,597 A | 7/1997 | Krapiva |
| 6,306,177 B1 | 10/2001 | Felt et al. |
| 6,383,190 B1 | 5/2002 | Preissman |
| 6,582,467 B1 | 6/2003 | Teitelbaum et al. |
| 6,733,505 B2 | 5/2004 | Li |
| 6,733,533 B1 | 5/2004 | Lozier |
| 6,740,093 B2 | 5/2004 | Hochschuler et al. |
| 6,764,514 B1 | 7/2004 | Li et al. |
| 6,852,095 B1 | 2/2005 | Ray |
| 7,081,120 B2 | 7/2006 | Li et al. |
| 7,128,746 B2 | 10/2006 | Singer et al. |
| 7,214,245 B1 | 5/2007 | Marcolongo et al. |
| 7,258,700 B2 | 8/2007 | Lambrecht et al. |
| 7,267,687 B2 | 9/2007 | McGuckin, Jr. |
| 7,473,256 B2 * | 1/2009 | Assell ................ A61B 17/1757 606/90 |
| 7,488,337 B2 | 2/2009 | Saab et al. |
| 7,491,236 B2 | 2/2009 | Cragg |
| 7,520,900 B2 | 4/2009 | Trieu |
| 7,628,800 B2 | 12/2009 | Sherman et al. |
| 7,641,691 B2 | 1/2010 | Lotz et al. |
| 7,699,894 B2 | 4/2010 | O'neil et al. |
| 7,799,078 B2 | 9/2010 | Embry et al. |
| 7,947,080 B2 | 5/2011 | Ferree |
| 7,976,578 B2 | 7/2011 | Marvel |
| 8,038,682 B2 | 10/2011 | McGill et al. |
| 8,287,595 B2 | 10/2012 | Vresilovic et al. |
| 8,292,961 B2 | 10/2012 | Osman |
| 8,529,628 B2 | 9/2013 | Marino et al. |
| 10,285,818 B2 | 5/2019 | Koss |
| 2002/0077701 A1 | 6/2002 | Kuslich |
| 2002/0147497 A1 | 10/2002 | Belef et al. |
| 2004/0030345 A1 | 2/2004 | Aurin et al. |
| 2004/0167625 A1 | 8/2004 | Beyar et al. |
| 2005/0043796 A1 | 2/2005 | Grant et al. |
| 2005/0113919 A1 | 5/2005 | Cragg et al. |
| 2005/0143826 A1 | 6/2005 | Zucherman et al. |
| 2005/0245938 A1 | 11/2005 | Kochan |
| 2005/0261781 A1 | 11/2005 | Sennett et al. |
| 2006/0079905 A1 | 4/2006 | Beyar et al. |
| 2006/0149380 A1 | 7/2006 | Lotz et al. |
| 2006/0247657 A1 | 11/2006 | Trieu |
| 2006/0293751 A1 | 12/2006 | Lotz et al. |
| 2007/0055201 A1 | 3/2007 | Seto et al. |
| 2007/0088436 A1 | 4/2007 | Parsons et al. |
| 2007/0173943 A1 | 7/2007 | Dulak et al. |
| 2007/0219490 A1 | 9/2007 | Pepper et al. |
| 2007/0276497 A1 | 11/2007 | Anderson |
| 2008/0009823 A1 | 1/2008 | McKay |
| 2008/0071356 A1 | 3/2008 | Greenhalgh et al. |
| 2008/0091167 A1 | 4/2008 | Trieu |
| 2008/0103596 A1 | 5/2008 | Shikinami et al. |
| 2008/0140201 A1 | 6/2008 | Siad et al. |
| 2008/0147098 A1 | 6/2008 | Trieu |
| 2008/0249604 A1 | 10/2008 | Donovan et al. |
| 2009/0069850 A1 | 3/2009 | Fuerderer |
| 2009/0076610 A1 | 3/2009 | Afzal |
| 2009/0112323 A1 * | 4/2009 | Hestad ................ A61F 2/4611 606/279 |
| 2009/0131939 A1 | 5/2009 | Ahrens et al. |
| 2009/0149958 A1 | 6/2009 | Prewett et al. |
| 2009/0254186 A1 | 10/2009 | Tornier et al. |
| 2010/0076481 A1 | 3/2010 | Stephens et al. |
| 2010/0145454 A1 | 6/2010 | Hoffman |
| 2010/0168859 A1 | 7/2010 | Wardlaw |
| 2010/0168864 A1 | 7/2010 | White et al. |
| 2011/0046737 A1 | 2/2011 | Teisen |
| 2011/0184349 A1 | 7/2011 | McKay |
| 2011/0270399 A1 | 11/2011 | Yurek et al. |
| 2014/0180415 A1 | 6/2014 | Koss |

FOREIGN PATENT DOCUMENTS

| | | |
|---|---|---|
| WO | 2004064673 A2 | 8/2004 |
| WO | 2006115956 A1 | 11/2006 |
| WO | 2007009107 A2 | 1/2007 |
| WO | 2011057394 A1 | 5/2011 |
| WO | 2012064473 A1 | 5/2012 |

OTHER PUBLICATIONS

International Search Report with Written Opinion for related Application No. PCT/US2018/013578 dated Mar. 13, 2018 (16 Pages).
European Supplementary Search Report for EP Application No. 13867389.2 dated Aug. 22, 2016 (7 Pages).
Extended Search Report issued from the European Patent Office for related Application No. 18899340.6 dated Aug. 24, 2021 (11 Pages).

* cited by examiner

SPINAL DISC IMPLANT AND DEVICE AND METHOD FOR PERCUTANEOUS DELIVERY OF THE SPINAL DISC IMPLANT

CROSS-REFERENCE TO RELATED APPLICATIONS

This application is a continuation of U.S. patent application Ser. No. 16/961,758, filed on Jul. 13, 2020, which is a national phase filing under 35 U.S.C. § 371 of International Application No. PCT/US2018/013578, filed Jan. 12, 2018, the entire contents of each application are incorporated herein by reference.

BACKGROUND OF THE INVENTION

The human spine is made up of consecutively aligned vertebral bodies. Each pair of adjacent vertebral bodies is separated and supported by an intervertebral disc positioned therebetween. Each intervertebral disc includes an annulus fibrosus which surrounds a central nucleus pulposus. Healthy discs are capable of carrying a tremendous load, as much as each adjacent vertebral body. The annulus fibrosis is made up of both Type 1 and Type 2 collagen having a lamellar formation with an alternating fiber orientation. The annulus fibrosis provides axial support with the help of the nucleus pulposus, which helps maintain the normal height of the annulus fibrosis.

Back pain affects millions of people in the United States and is the number one cause of disability worldwide. In particular, low back pain affects about 31 million Americans at any given time, and 80% of people will experience low back pain at some point in their lifetime. Back pain has a variety of causes, with one of the most common causes of back pain being disc degeneration. Aging causes the disc, specifically the nucleus pulposus, to begin to desiccate or lose water. As the nucleus desiccates, it changes shape and loses height, transferring increasing load to the annulus which begins to weaken. A weakened annulus is susceptible to annular failure, which results in tears, bulges, and herniations of the annulus. Weakening of the components of the disc eventually causes increased deformation of the disc, which further weakens the annulus. The end stage of this cycle of deterioration is the complete loss of disc height, end plate bone spur formation, and facet hypertrophy.

Currently, there are several ways to manage the pain associated with disc degeneration. The most conservative approach is to use pain medications such as NSAIDS, steroid packs, and narcotics. Most often, these medications are administered in conjunction with both physical and massage therapy. An alternative and common conservative approach is epidural steroid injections. Back pain can also be mitigated by a minimally invasive procedure known as intradiscal electrothermal therapy (IDET). IDET includes thermal repair of the inner annulus fibrosus, repairing collagen and ultimately stimulates collagen synthesis. IDET can cause retraction of the herniated disc and improve low back pain, but does nothing to address the weakened and failing nucleus pulposus. While IDET results in statistically significant pain and disability improvement, is more effective on patients with greater disability at the onset of treatment and therefore is a worthwhile intervention for some highly select patients. More aggressive treatment of back pain includes one of several lumbar spine surgeries such as a microdiscectomy, a laminectomy, a posterior fusion, an anterior inter-body fusion, a disc annuloplasty, or a foraminotomy. While surgery is a viable option as a solution for back pain, it incurs very high medical expenses, has inherent associated surgical risks, in-hospital recovery, and a high failure rate. As a result, better solutions for treating back pain are needed.

SUMMARY OF THE INVENTION

One solution is to treat degenerative disc disease with a less invasive solution without the severe risks, prolonged recovery time, and expense associated with current surgical implants and techniques. Therefore, one embodiment of the present invention is a device and method for replacement of the nucleus pulposus. Replacing the nucleus pulposus restores strength to the central disc and restores height of the annulus for improved structural integrity of the spine such that the cycle of back pain described above is not perpetuated. A second embodiment of the present invention is a device and method for a minimally invasive lumbar inter-body fusion.

In one embodiment, the invention provides a spine implant comprising a plurality of braided nitinol strands, the braided nitinol strands including a slight hour-glass like configuration, a first fitting configured to secure first ends of the plurality of braided nitinol strands, and a second fitting opposite the first fitting, the second fitting configured to secure second ends of the plurality of braided nitinol strands, the second fitting possibly including a snare hook.

In another embodiment, the invention provides a spine implant comprising a body composed of a plurality of braided nitinol strands defining a first end, a second end, and an interior cavity, a coating that can be applied to the braided nitinol skeleton to provide an impervious barrier to liquids or gel-like substances from exiting the interior cavity when serving as a nucleus pulposus implant, a first fitting coupled to the first end and configured to be embedded in the inferior aspect of the vertebral body adjacent to the degenerated disc, a body of the implant situated in the degenerated disc space, and a second fitting coupled to the second end and configured to be embedded in the superior aspect of the vertebral body adjacent to the degenerated disc.

In a further embodiment, the invention provides a device for positioning a spinal implant using a trans-osseous (i.e., trans-pedicular) method for positioning, deploying and fully expanding the implant while leaving the outer annular fibers intact. The device comprises a first coupling (bonded to the pusher tube) removably coupled to a spine implant, the first coupling including a threaded bore, a second coupling (bonded to the first end of the spine implant) removably coupled to the first coupling, the second coupling including a female threaded end configured to be received by the threaded bore of the first coupling, a hollow pusher tube configured to move the spinal disc implant out of a cannula and into position between a first vertebral body and a second vertebral body adjacent to the first vertebral body within the disc space, and a hollow pusher tube connected to an infusion port for filling the implant with liquid, gel, silicone, bone graft material or other medical grade fillers.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected," "supported," and "coupled" and variations thereof are used broadly and encompass both direct and indirect connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

Figure 1:
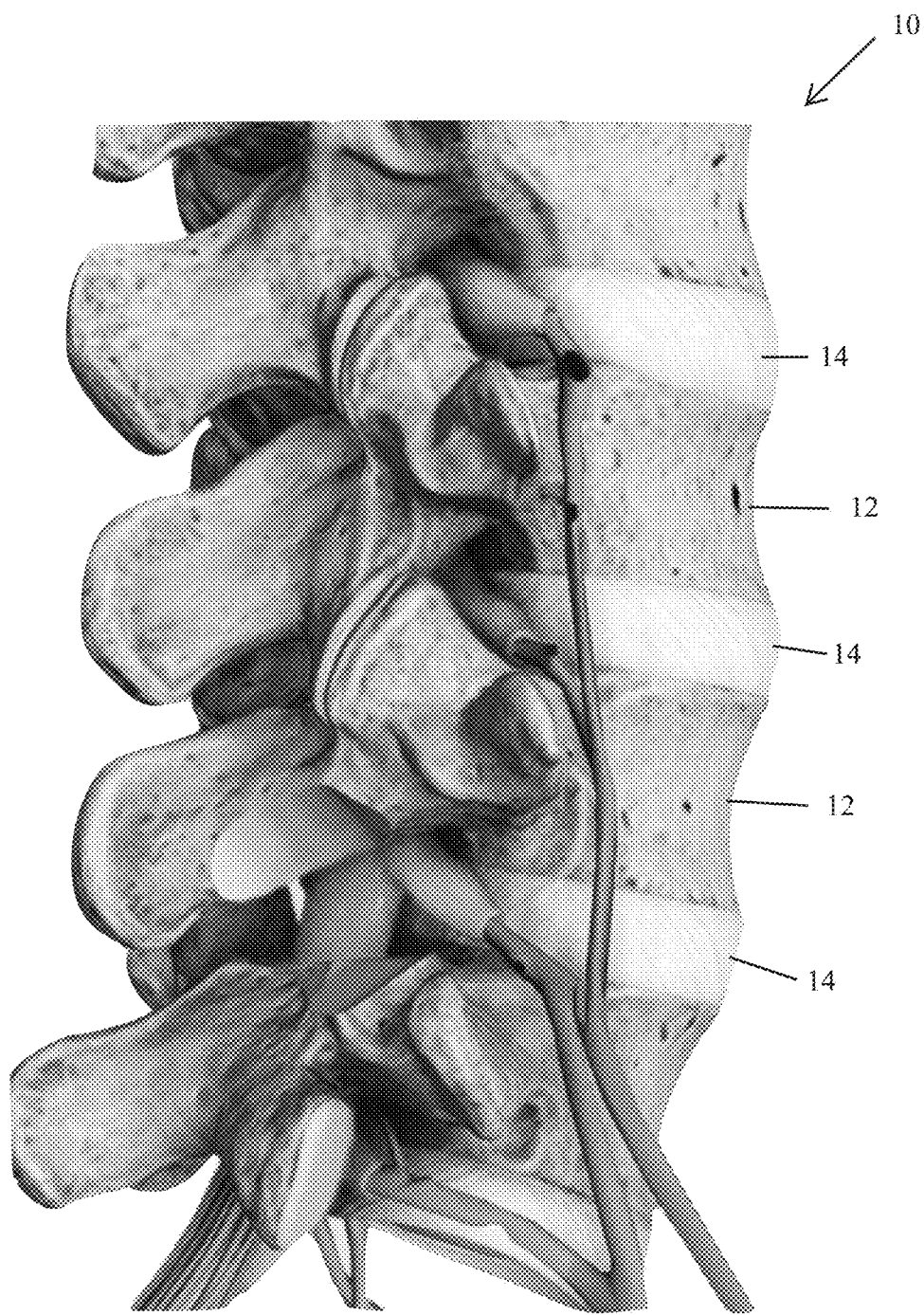
FIG. 1 is a lateral view of the human spine with nerves.
Figure 2:
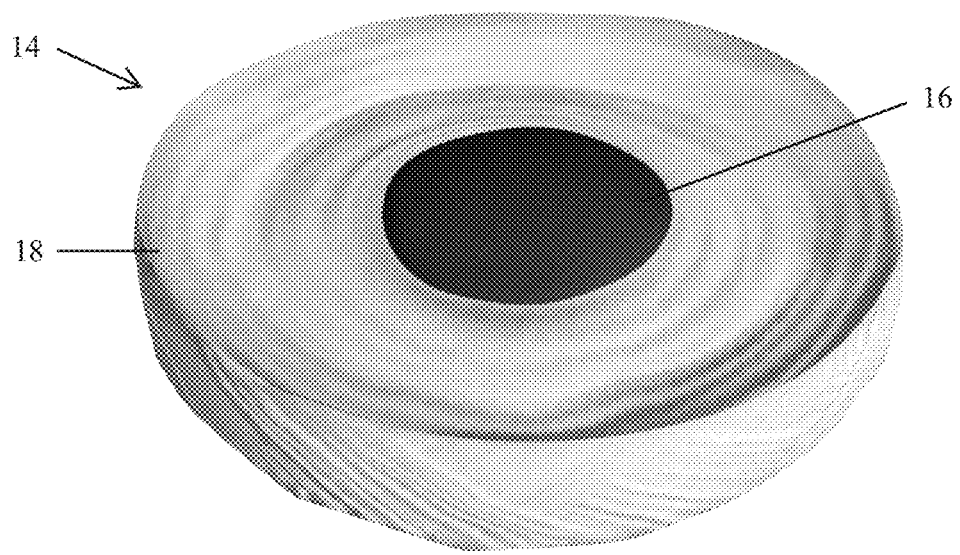
FIG. 2 illustrates a human lumbar disc with annulus fibrosus and nucleus pulposus.

FIG. 1 illustrates the human spine 10. The human spine 10 is made up of consecutively aligned vertebral bodies 12 (i.e., vertebrae). Adjacent vertebrae 12 are separated by an intervertebral disc 14 as shown in FIG. 2. The intervertebral discs 14 are avascular, fibrocartilaginous structures that act as load bearing shock absorbers, yet flexible structures providing mobility to the spine. With reference to FIG. 2, each disc 14 includes a nucleus pulposus 16 that is enclosed within an annulus fibrosus 18. The nucleus pulposus is a soft, gel-like substance. The annulus fibrosus 18 is made up of circumferential rings with collagen having an alternating fiber orientation. The annulus fibrosus is strongest when its height is maintained. Under normal conditions, the nucleus pulposus 16 helps maintains the vertical height of the annulus fibrosus 18 such that together, the nucleus pulposus 16 and the annulus fibrosus 18 provide tremendous axial support to the spine 10.

Figure 3:
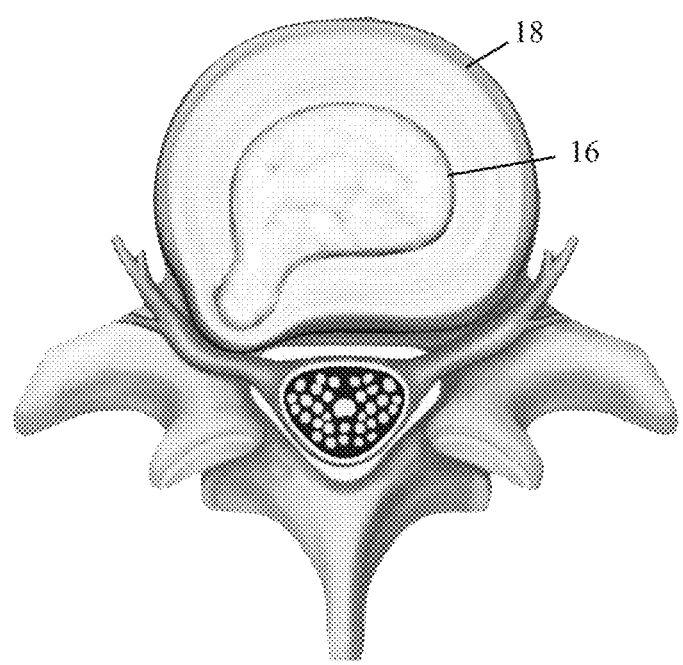
FIG. 3 is an axial view of the human lumbar spine showing disc herniation.

FIG. 3 illustrates a disc herniation where there is a tear in the annulus fibrosus 18 that allows the nucleus pulposus 16 to bulge out beyond the damaged annulus fibrosus 18. Disc herniation is usually due to age-related disc degeneration. A tear in the annulus fibrosus and resulting disc herniation results in the release of chemicals causing inflammation and mechanically compressing the adjacent nerve roots causing severe pain.

Figure 4:
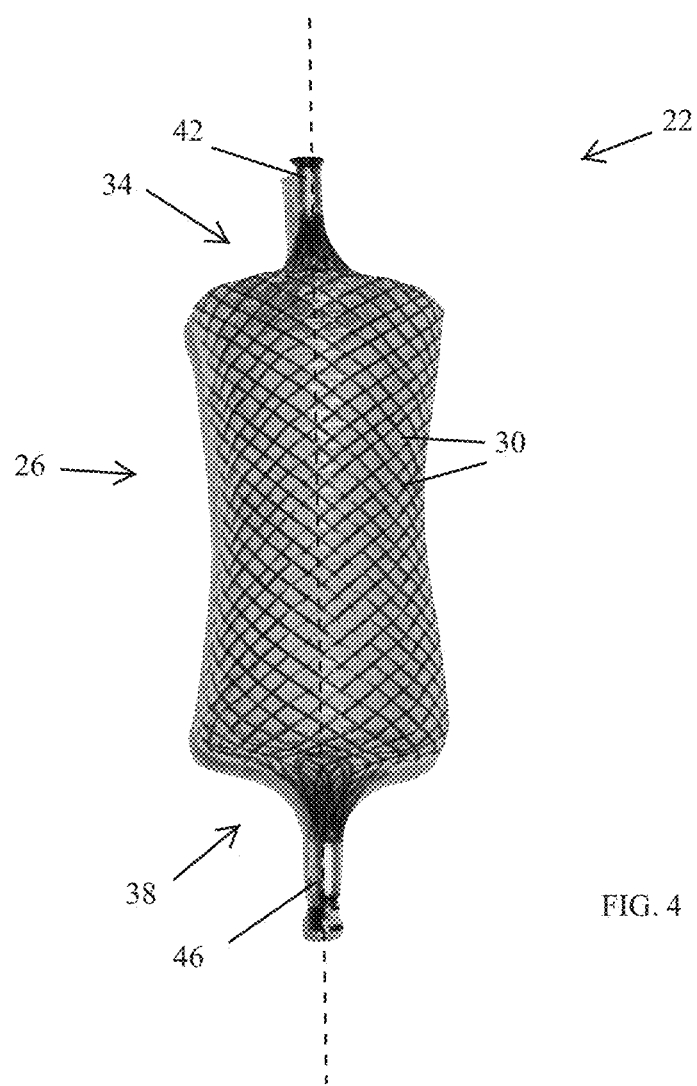
FIG. 4 illustrates a spinal implant according to an embodiment of the present invention.

FIG. 4 illustrates a spinal implant 22 according to an embodiment of the present invention. The spinal disc implant 22 provides a minimally invasive "needle based" solution to address degenerative disc disease, reduces the risk of nerve damage, maintains spine mobility (when used as a nucleus pulposus implant), and provides enhanced structural integrity to the spine. The spinal disc implant 22 is capable of being positioned and assembled within the intervertebral disc 14. When in use, the implant 22 replaces the nucleus pulposus 16 at a portion of the inner fibers of the annulus fibrosus 18.

Figure 5:
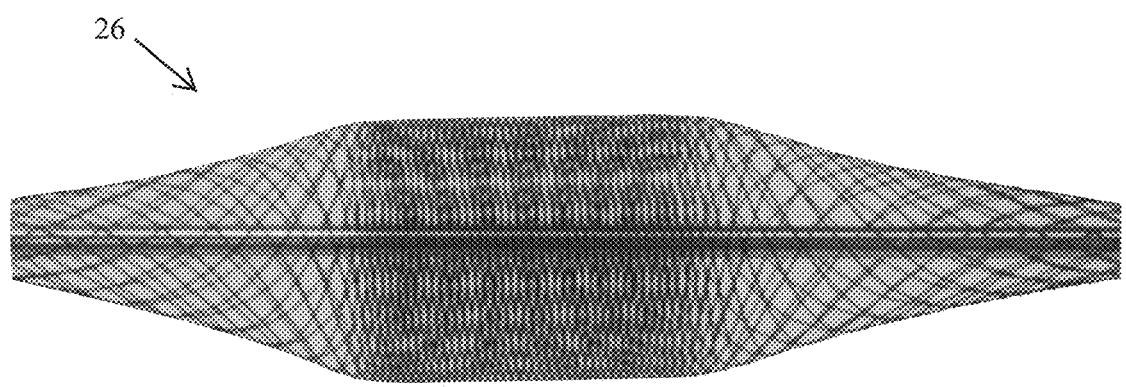
FIG. 5 illustrates a braid structure of the spinal implant illustrated in FIG. 4.
Figure 6:
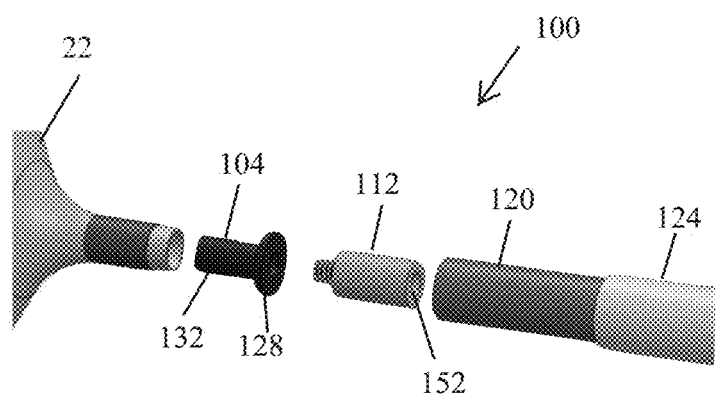
FIG. 6 is an exploded view of a delivery device for placement of the spinal implant illustrated in FIG. 4.
Figure 7:
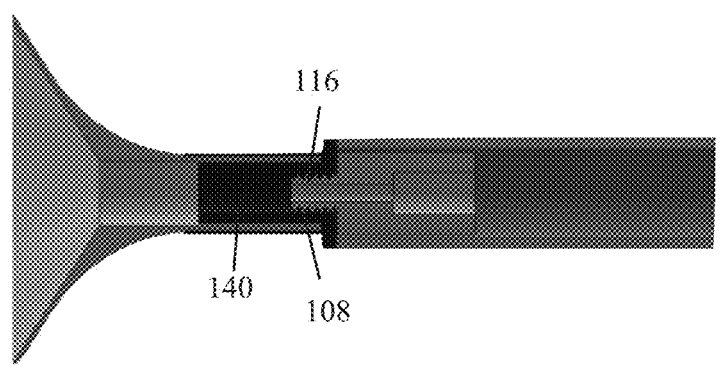
FIG. 7 is a side cross-sectional view of the delivery device shown in FIG. 6.
Figure 8:
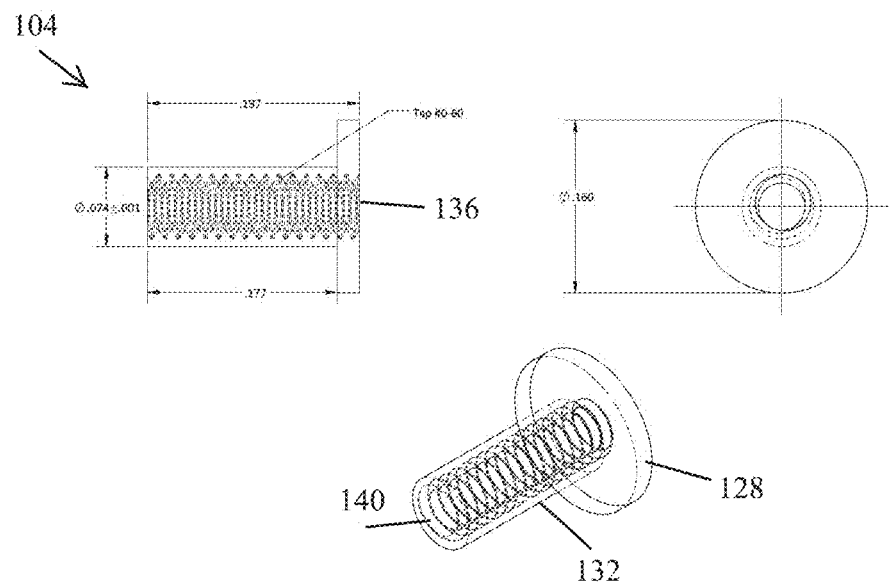
FIG. 8 illustrates several views of a component of the delivery device shown in FIGS. 6-7.
Figure 9:
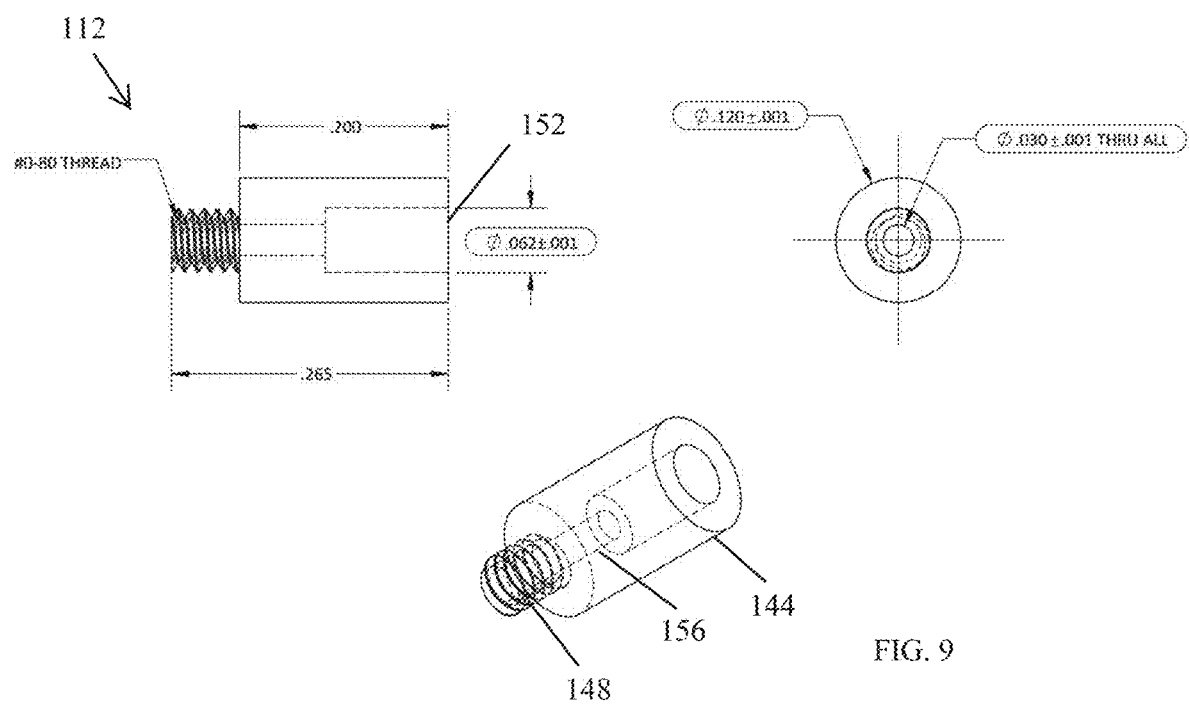
FIG. 9 illustrates several views of a component of the delivery device shown in FIGS. 6-7.
Figure 10:
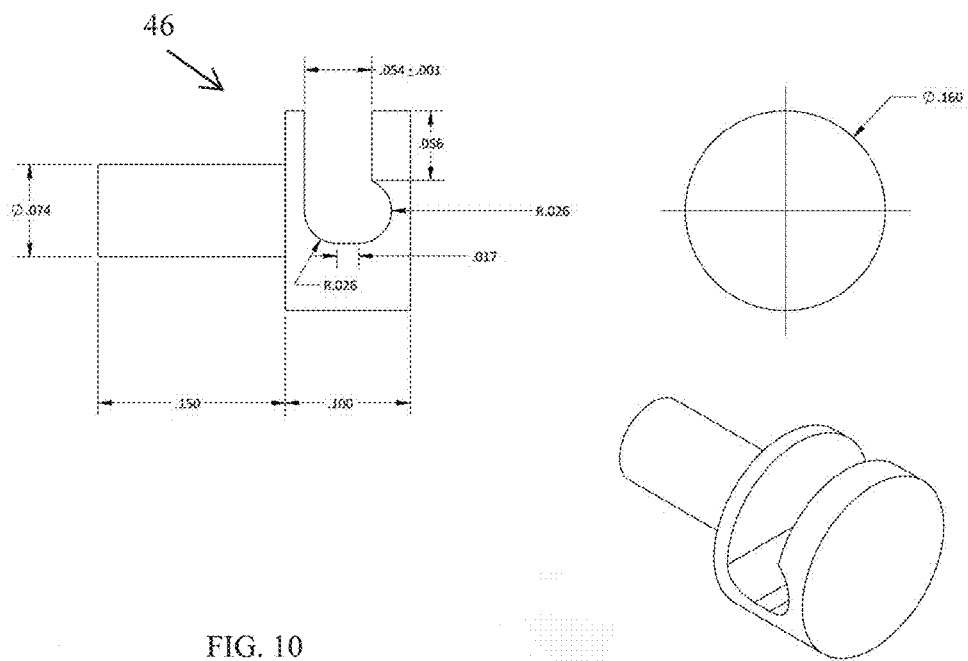
FIG. 10 illustrates several views of a component of the spinal disc implant illustrated in FIG. 4.

The spinal implant 22 includes a body 26 or a skeleton defined by a plurality of interwoven or braided nitinol strands 30. FIG. 5 further illustrates the braiding pattern of the nitinol strands 30. The body 26 includes a first end 34 and a second end 38. In between the first end 34 and the second end 38 is a middle cavity. The nitinol strands 30 come together at the first end 34 and are secured with a first fitting 42. The nitinol strands 30 also come together at the second end 38 and are secured with a second fitting 46. The second fitting 46 can comprise a snare hook as further illustrated in FIG. 10. In some constructions, both the first end 34 and the second end 38 can comprise a snare hook.

Figure 20:
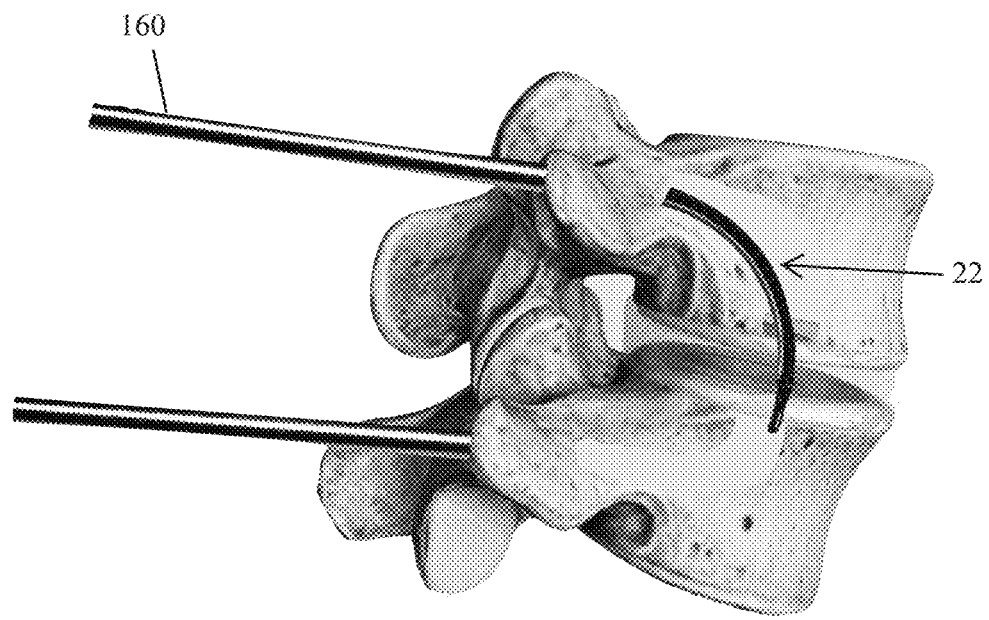
FIG. 20 illustrates a side view of a portion of the human spine showing positioning of the spinal implant with the second fitting secured within the superior endplate of the inferiorly positioned vertebral body.
Figure 21:
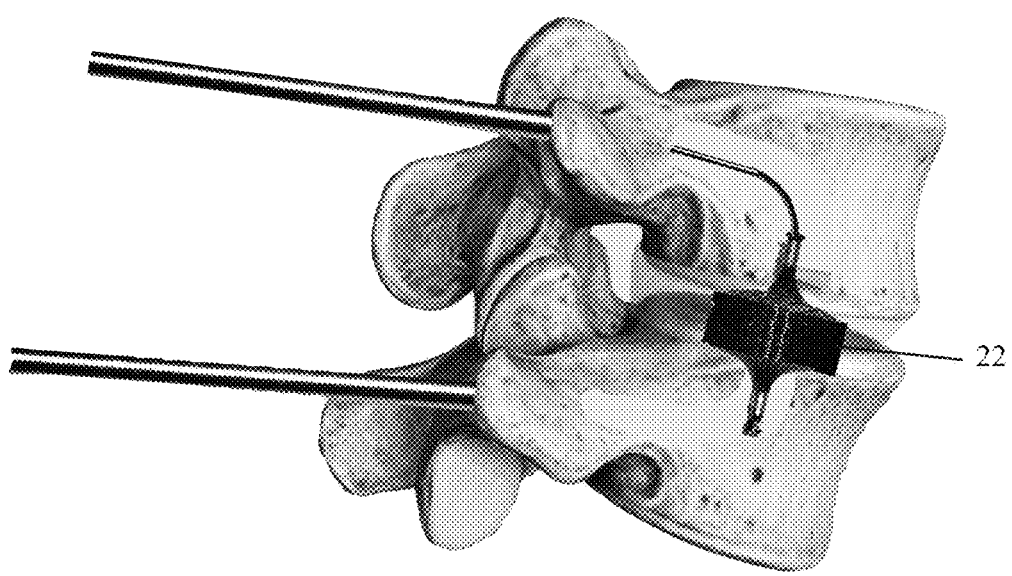
FIG. 21 illustrates a side view of a portion of the human spine showing deployment of the spinal implant with each fitting of the implant secured in their respective vertebral body endplates.
Figure 22:
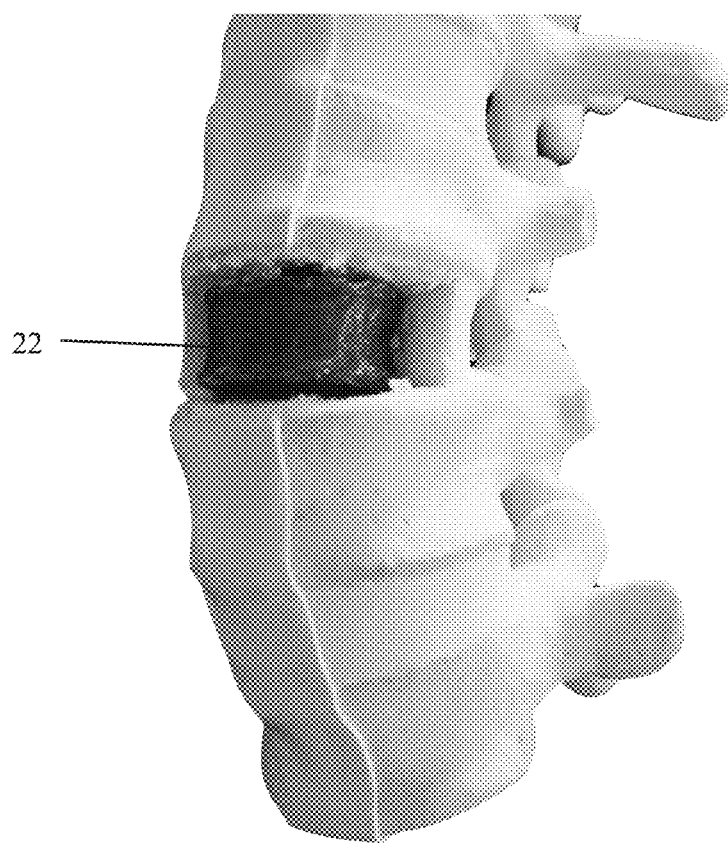
FIG. 22 illustrates a side view of a portion of the human spine showing the spinal implant in position and filled with medical grade silicone.

As illustrated in FIG. 4, the body 26 defines a longitudinal axis extending through the first end 34 and the second end 38. The body 26 forms a slight hour-glass like shape in its unconstrained configuration for greater cross-sectional coverage and therefore a broader distribution of load forces. The middle portion includes a diameter that is slightly less than the diameter of the first end 34 or the second end 38. In some constructions, the diameter of the body 26 gradually decreases from the first end 34 to the middle portion, and the diameter of the body 26 gradually decreases from the second end 38 to the middle portion. The spinal implant 22 is flexible and can change shapes when a compressive force or a tensile force is applied to the ends 34, 38. For example, when a compression force is applied to the first end 34 and the second end 38, the implant 22 moves to an unconstrained state as shown in FIGS. 20-22. Additionally, when a tensile force is applied to the first end 34 and the second end 38, the implant 22 moves to an elongated and more narrow diameter state allowing the implant to be constrained to a small diameter for needle/cannula based delivery, as shown in FIG. 5.

The braided nitinol strands 30 can be coated such that the coating covers the spaces between the nitinol strands 30 to thereby form a cavity 50, which is impervious to liquids or gel-like substances from exiting the cavity 50 when used as a nucleus pulposus implant. In one construction, the coating is silicone.

With reference to FIGS. 6-13, the implant 22 is positioned in the intervertebral disc 14 (i.e., the space encompassed by the nucleus pulposus and inner annular fibers) with a delivery device or instrument 100. The instrument 100 includes a first coupling 104, a second coupling 112 and a pusher tube 120. The first coupling 104 is bonded to the first fitting 42 of the implant 22. The first coupling 104 includes a circular head 128 and an extension 132. The circular head 128 includes an opening 136 therethrough that continues through a bore 140 in the extension 132. The interior surface of the opening 136 and the bore 140 are threaded. The threaded female end (see FIG. 8) receives a threaded male portion of the second coupling 112. The second coupling 112 includes a threaded male end 116 (see FIG. 9) to be threadingly received within the threaded female end of the first coupling 104. The second coupling 112 includes a bore 152 and is in fluid communication with the bore of the first coupling 104. The second coupling 112 is bonded to a pusher tube 120 configured to fit within a sheath 124 for supporting and positioning the implant 22. The opening 136 of the first coupling 104 is configured to removably receive the second coupling 112. The second coupling 112 includes a base 144 and an extension 148. A distal end of the base 144 includes an opening 152 therethrough that continues through a bore 156 in the extension 148 such that the first coupling 104, the second coupling 112, and the implant 22 are in fluid communication through the first fitting 42 of the implant 22.

Figure 14:
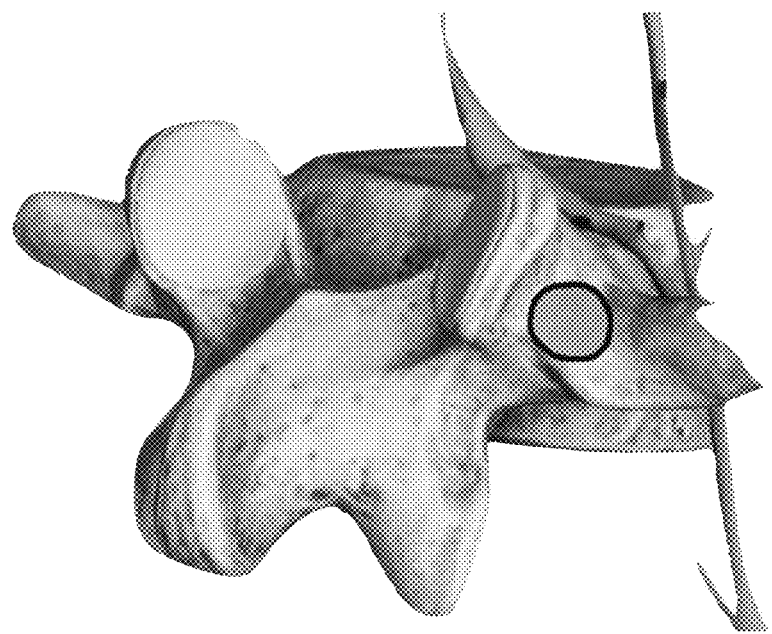
FIG. 14 illustrates a posterior oblique view of a portion of the human spine for initial transpedicular access into the vertebral body above the degenerated lumbar disc.
Figure 15:
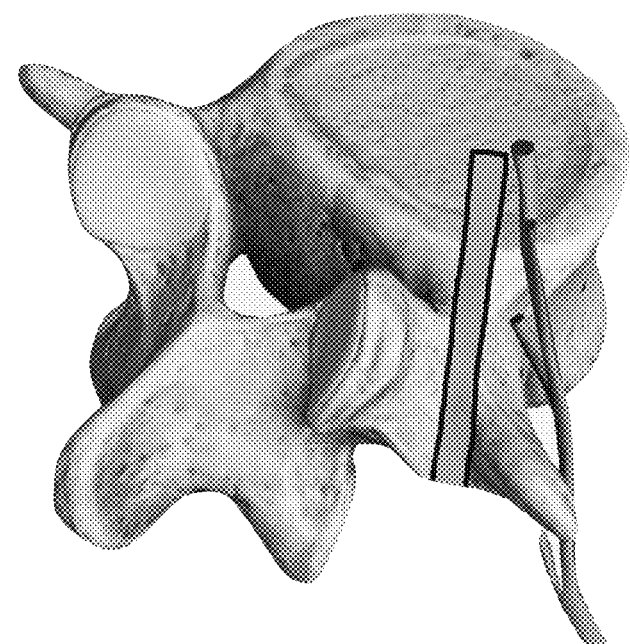
FIG. 15 illustrates a top perspective view of a portion of the human spine for initial transpedicular access into the vertebral body above the degenerated lumbar disc.
Figure 16:
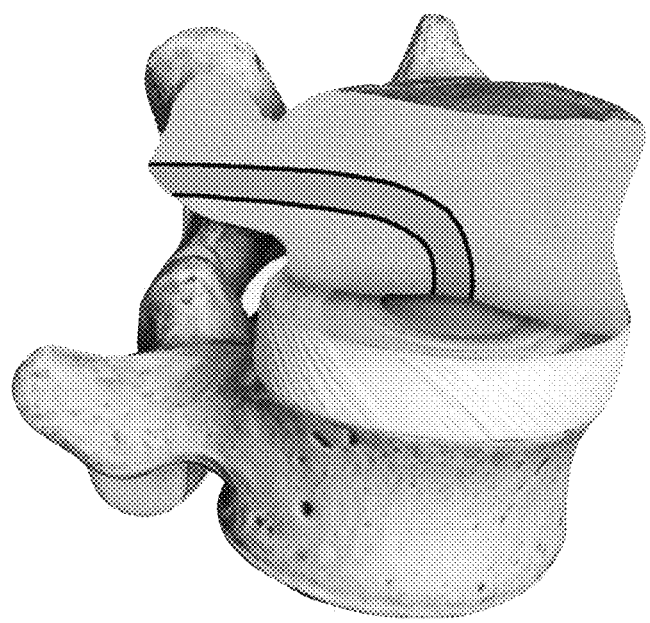
FIG. 16 illustrates a side view of a portion of the human spine for transpedicular access into the degenerated lumbar disc.
Figure 17:
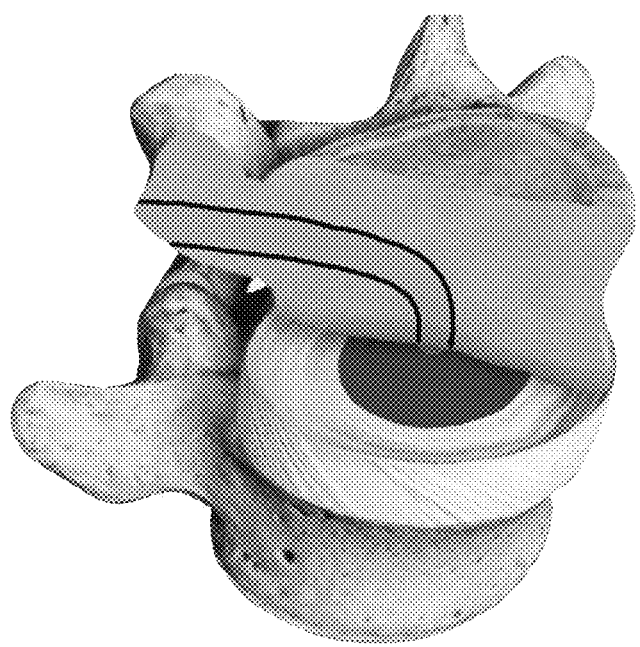
FIG. 17 illustrates a side view of a portion of the human spine with transpedicular access to the degenerated lumbar disc and removal of the degenerated nucleus and inner annular fibers in preparation for implant delivery.
Figure 18:
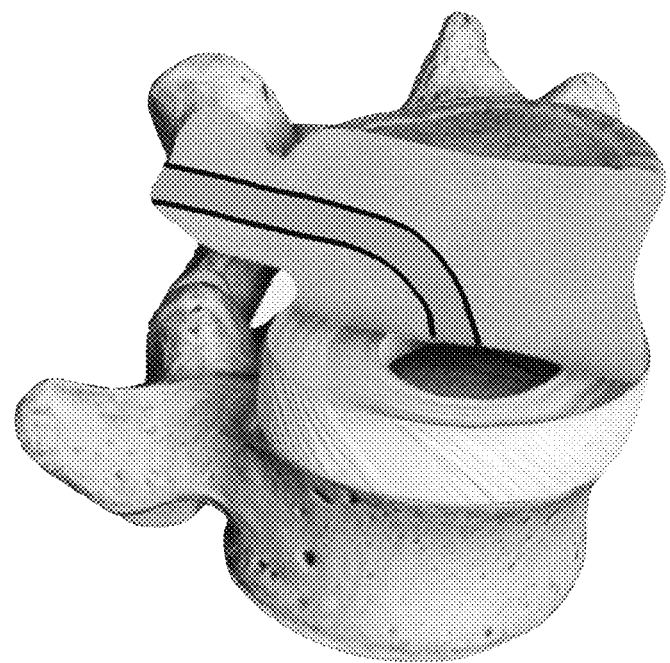
FIG. 18 illustrates a side view of a portion of the human spine with access to the lumbar disc and showing completed preparation of the disc for positioning of the spinal implant.

FIGS. 14-21 illustrate a method for positioning the implant 22 in the intervertebral disc 14. The method can be performed as an outpatient procedure with intravenous sedation, MAC or general anesthesia. The method begins with a percutaneous and fluoroscopic-guided transpedicular (or transosseous) access into the intervertebral disc and placement of an introducer cannula 160. Initially, access to the intervertebral disc 14 of interest is provided by drilling an access channel into the superiorly positioned vertebral body to access the disc 14 in a transpedicular (or transosseous) manner. FIGS. 14-15 illustrate the access channel that provides transpedicular (or transosseous) access to the intervertebral disc 14. The intervertebral disc 14 is prepared with radiofrequency augmentation to facilitate removal of the degenerated nucleus and promoting collagen repair and strengthening of the remaining annular fibers. The degenerated or damaged nucleus pulposus 16 is removed percutaneously using thermal ablation and mechanical extraction devices. Additional arthroscopic tools can be used to further prepare the disc space, decompress disc herniations, and debride the cartilaginous endplates of the adjacent vertebral bodies when using the implant for inter body fusion. FIGS. 16-18 schematically illustrate removal of the nucleus pulposus 16 and preparation of the disc space for receipt of the implant 22.

Figure 11:
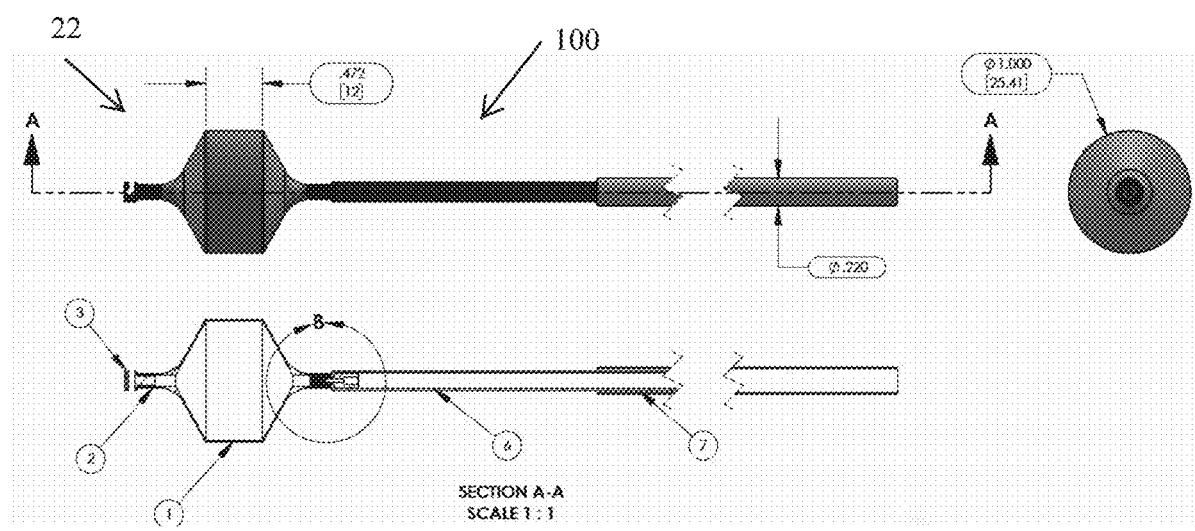
FIG. 11 illustrates several views of the device shown in FIGS. 6-7 with the spinal disc implant illustrated in FIG. 4 coupled thereto.
Figure 12:
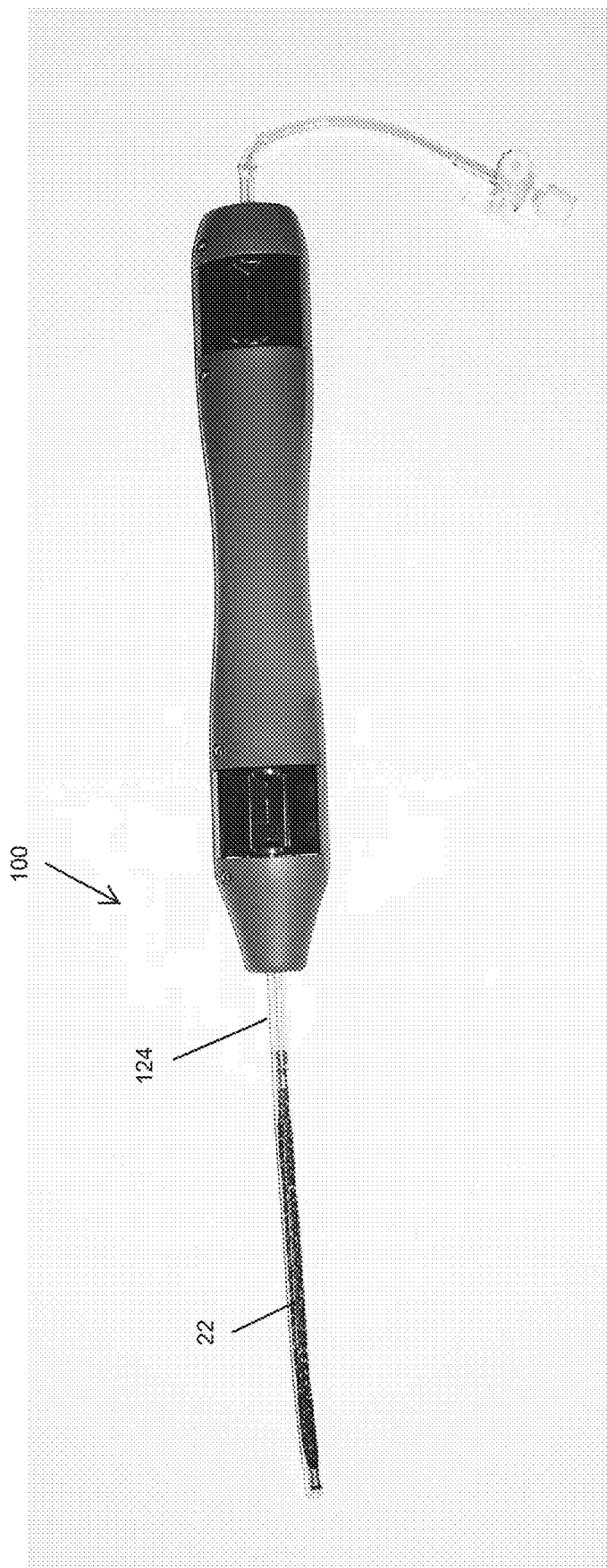
FIG. 12 illustrates the spinal disc implant constrained in the delivery device shown in FIGS. 6-7.
Figure 13:
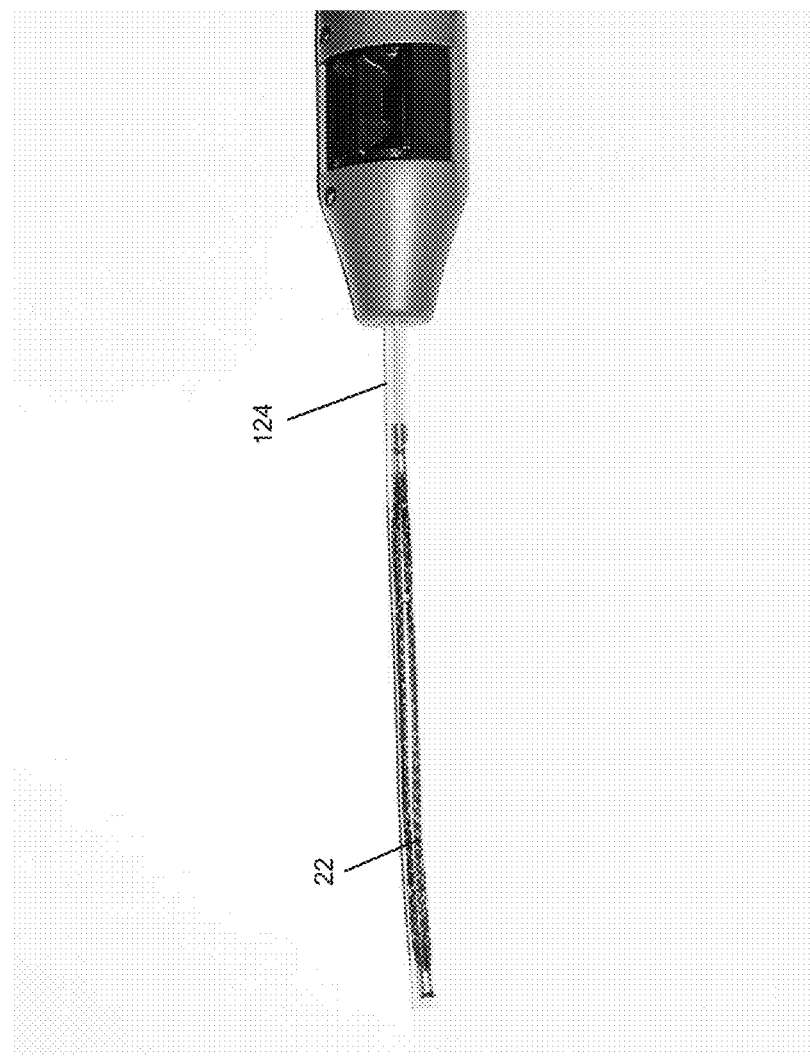
FIG. 13 illustrates an enlarged view of the spinal disc implant constrained in the delivery device shown in FIG. 12.
Figure 19:
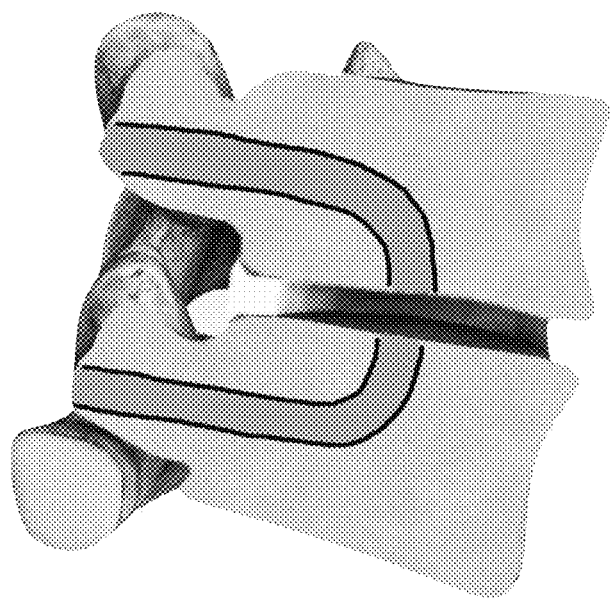
FIG. 19 illustrates a side view of a portion of the human spine with superior and inferior access to the lumbar disc and showing completed preparation of the disc for positioning of the spinal implant.

The implant 22 is pre-mounted onto the distal end of the instrument 100. The first coupling 104 is temporarily coupled to the second coupling 112 as illustrated in FIG. 11. The pusher tube 120 is retracted to apply a tensile force to the first fitting 42 of the implant 22 to thereby stretch and retract the implant 22 into the sheath 124. Access into the disc space from both the superior and inferior vertebral bodies adjacent to the disc may facilitate disc preparation and delivery of the second fitting 46 into the inferiorly positioned vertebral body as illustrated in FIG. 19. With reference to FIGS. 20-21, the cannula 160 is flexible to enter the access channel through the intervertebral body. The constrained implant 22 and sheath 124 are delivered through the channel, traversing the central portion of the disc and seating the second fitting 46 into the inferiorly positioned vertebral body. The implant 22 is delivered with a combination of sheath 124 retraction and implant 22 pushing with the pusher tube 120 through the space where the nucleus pulposus and inner annular fibers were removed. The second fitting 46 extends through the open space and comes into contact with and is embedded into the adjacent vertebral body. The second fitting 46 can be configured with a snare hook end facilitating delivery of the implant 22 into the inferiorly positioned vertebral body. The snare hook end is embedded into the vertebral body such that the implant 22 remains in position and is less prone to migration or expulsion.

Figure 23:
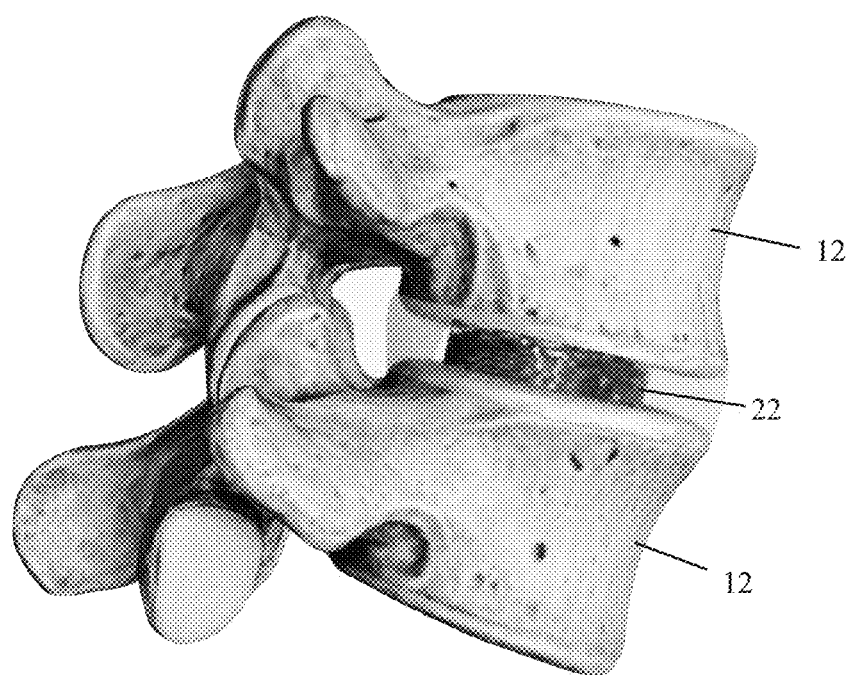
FIG. 23 illustrates a lateral view of a portion of the human spine showing the spinal implant in position.
Figure 24:
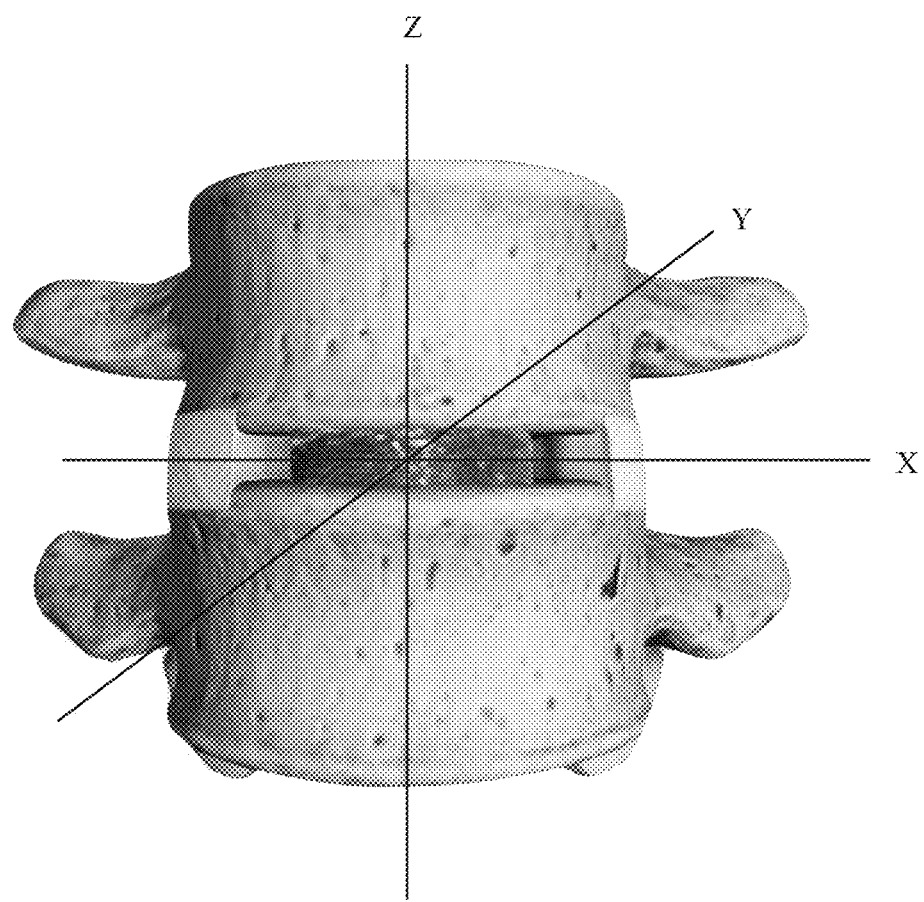
FIG. 24 illustrates an anteroposterior view of a portion of the human spine showing the spinal implant in position.

The retractable sheath 124 from the delivery system 100 is then completely retracted to release the implant 22 into the open space in the intervertebral disc with the first fitting 42 remaining within the distal end of the retractable sheath 124. The implant 22 remains contained within the central disc space as illustrated in FIG. 21 upon full release of the implant 22. The implant 22 remains constrained due to the space or distance between the two adjacent vertebral bodies. The space or distance is less than the length of the implant 22 in the unconstrained state. The diameter of the implant is dimensioned to be similar to the diameter of the open space where the nucleus pulposus and inner annular fibers were removed. While the instrument 100 is still coupled to the implant 22, the cavity of the implant may be injected with a substance through the hollow pusher tube 120, through the second coupling 112 to the implant 22, and filling the implant 22 to its complete state with full expansion in the Z axis. The implant 22 is filled with liquid, gel, silicone, or bone graft materials. After complete deployment and filling of the implant 22, the second coupling 112 of the delivery instrument 100 is rotatably detached from the first fitting 42 on the first end of the implant 22 and is retracted from the access cannula 160. Bone graft material or methymethacrylate can then be injected through the access cannula 160 to fix the first and second fittings in their respective vertebral bodies. FIGS. 22-24 illustrate the implant 22 in position. The implant 22 replaces a degenerated nucleus pulposus and restores the annular height for improved structural integrity.

The implant 22 can also be used as an internally assembled inter-body fusion implant when using a non-coated nitinol skeleton and filling the implant with bone graft material.

It is noted that this implant 22 is in contrast to other implants that have no endoskeleton beyond that of the outer wall (such as in a balloon). The implant 22 is not a simple balloon, but rather an internally assembled device constrained in the XY plane and secured within the adjacent endplates of the adjacent vertebral bodies. The diameter and height of the implant 22 is customized to the patient's anatomy based on pre-operative MR imaging. The XY constraint is important, as a simple balloon may not have as accurate a shape as desired. The filling of the implant 22 will then complete the shape of the implant 22 and specifically provide shape and support in the Z axis (cranial and caudal). See FIG. 22 for reference coordinates.

To demonstrate the capability of the implant 22, it was axially load tested to determine the compressive load it could withstand. The implant 22 was capable of handling 450 lbf (2.0 kN). These measurements indicate that the implant 22 performs above ASTM standards.

Various features and advantages of the invention are set forth in the following claims.

What is claimed is:

1. A spinal disc implant comprising:
    a body comprising a plurality of braided nitinol strands defining a first end, a second end, and an interior cavity;
    a coating applied to the body to provide an impervious barrier to liquids or gel-like substances from entering the interior cavity;
    a first fitting coupled to the first end and configured to be embedded in a first vertebral body; and
    a second fitting coupled to the second end and configured to be embedded in a second vertebral body adjacent to the first vertebral body.

2. The spinal disc implant of claim 1, wherein the coating is silicone.

3. The spinal disc implant of claim 1, wherein a middle portion of the implant includes a first diameter, and wherein the first end includes a second diameter, and further wherein the first diameter is less than the second diameter.

4. The spinal disc implant of claim 1, wherein the first end includes a first diameter, and wherein the second end includes a second diameter, and further wherein the first diameter is the same as the second diameter.

5. The spinal disc implant of claim 1, wherein the plurality of braided nitinol strands is flexible such that the implant stretches and lengthens when a tensile force is applied to the first fitting and the second fitting.

6. The spinal disc implant of claim 1, wherein the plurality of braided nitinol strands is flexible such that the implant is self-expanded when a compression force is applied to the first fitting and the second fitting.

7. A device for positioning a spinal disc implant, the device comprising:
    a pusher tube;
    a first coupling bonded to a spinal disc implant, the first coupling including a threaded bore;
    a second coupling comprising a cylindrical body and a threaded end extending distally from the cylindrical body, wherein the cylindrical body is bonded within a lumen of the pusher tube such that a distal end of the cylindrical body is flush with a distal end of the pusher tube, and wherein the threaded end extends distally from the distal end of the pusher tube, is removably coupled to the first coupling, and is configured to be received by the threaded bore of the first coupling; and
    the pusher tube being configured to move the spinal disc implant out of a cannula and into position between a first vertebral body and a second vertebral body adjacent to the first vertebral body.

8. The device of claim 7, wherein the second coupling includes a bore therethrough such that the bore is in fluid communication with the threaded bore of the first coupling.

9. The device of claim 7, wherein the pusher tube is hollow so as to deliver liquids, gels, silicone or bone graft material from a delivery handle through the first and second couplings and into an interior chamber of the spinal disc implant.

* * * * *